United States Patent [19]

Giffard

[11] Patent Number: 4,723,542

[45] Date of Patent: Feb. 9, 1988

[54] BREATHING MASK AND ITS PRODUCTION PROCESS

[75] Inventor: Louis Giffard, Languex, France

[73] Assignee: L. Giffard, S.A., Plaintel, France

[21] Appl. No.: 838,700

[22] Filed: Mar. 12, 1986

[51] Int. Cl.[4] .................. A61F 5/56

[52] U.S. Cl. .................. 128/136

[58] Field of Search .............. 128/136, 205.28, 206.15, 128/206.19

[56] References Cited

U.S. PATENT DOCUMENTS

| | | | |
|---|---|---|---|
| 2,120,230 | 6/1938 | Cover | 128/146 |
| 2,798,483 | 7/1957 | Kashima | 128/206.15 |
| 3,633,575 | 1/1972 | Brumfield | 128/206.15 |
| 4,573,464 | 3/1986 | Yo | 128/206.15 |
| 4,600,002 | 7/1986 | Maryyanek et al. | 128/206.19 |

FOREIGN PATENT DOCUMENTS

| | | |
|---|---|---|
| 2430774 | 8/1980 | France . |
| 2077112 | 12/1981 | United Kingdom . |

*Primary Examiner*—Robert A. Hafer

*Assistant Examiner*—Danton D. DeMille

*Attorney, Agent, or Firm*—Fisher, Christen & Sabol

[57] ABSTRACT

The mold has three layers of shrinkable material. The outside layer is provided with a plurality of recesses arranged as a fan. A granular filtering material is compressed in the recesses of layer closed by layer, during a later thermal operation, for example, a shaping of the mask.

16 Claims, 2 Drawing Figures

BREATHING MASK AND ITS PRODUCTION PROCESS

BRIEF DESCRIPTION OF THE INVENTION

1. Field of the Invention

The invention relates to a new disposable breathing mask whose filtering element consists of a granular material, for example activated carbon in granular form. The invention also relates to a production process for such new disposable breathing mask.

2. Prior Art

French Pat. No. 2,158,629 describes a filtering element consisting of a bowl having approximately the shape of a yoghurt pot whose strap is stiffened and closed after complete filling by a bottom made of a heat-shrinkable material so that, after shrinking, the activated carbon, contained in the bowl, is compressed because of the reduction in volume. The filtering elements are used in industry, for example, in a fluid transportation pipe, the large surface of the bowl being turned upstream so that the fluid stream encounters a filtering mass that is increasingly compressed as it approaches the shrunken bottom, thus accentuating the packing of the carbon.

Activated carbon masks are difficult to make to be effective for an acceptable period of time because of the limitation of the amount of carbon. For this reason, there are only a few disposable models; Masks with replaceable carbon cartridges are preferred, but which, because of their small filtering surface does not rule out their rapidly becoming saturated.

BROAD DESCRIPTION OF THE INVENTION

The invention provides a solution to this problem by increasing the exchange surface and, consequently, the weight of the filtering mass, by fragmenting it into multiple portions to take into account that a compression of carbon is effective only when the enclosure containing the filtering mass is only of a limited volume.

BRIEF DESCRIPTION OF THE DRAWINGS

Other features and advantages of the mask and process of the invention are shown by the following description and claims, with particular reference to the accompanying drawings in which:

DETAILED DESCRIPTION OF THE INVENTION

Figure 1:
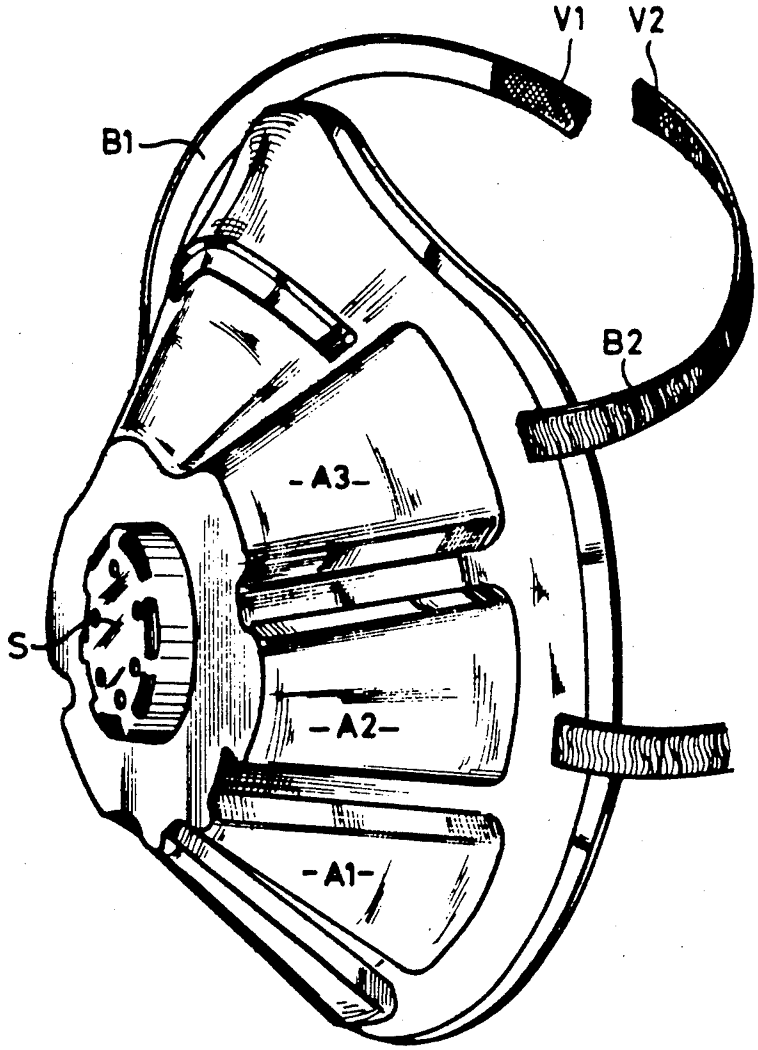
FIG. 1 is a perspective view of a mask according to the invention.

As can be seen in FIG. 1, the mask is in the form of shell C whose periphery closely fits the user's face by a strap in the form of two elements B1–B2 joining behind his neck by means of two complementary elements V1–V2 formed by a self-hooking material, such as that sold under the trademark VELCRO. According to the invention, shell C is provided with a plurality of recesses A1–A2 . . . A6 projecting outstanding on its front face. Each recess is in the shape of a truncated pyramid or truncated cone. Advantageously, these recesses are arranged so as to radiate in the direction of the foremost part of the snout, whether they meet at this point or end in circular recess or in a central valve S of the outlet of the expired air. Each recess is filled with grains of a filtering material (activated carbon, for example) which are compressed, for example, by heat-shrinking of the material constituting shell C.

Figure 2:
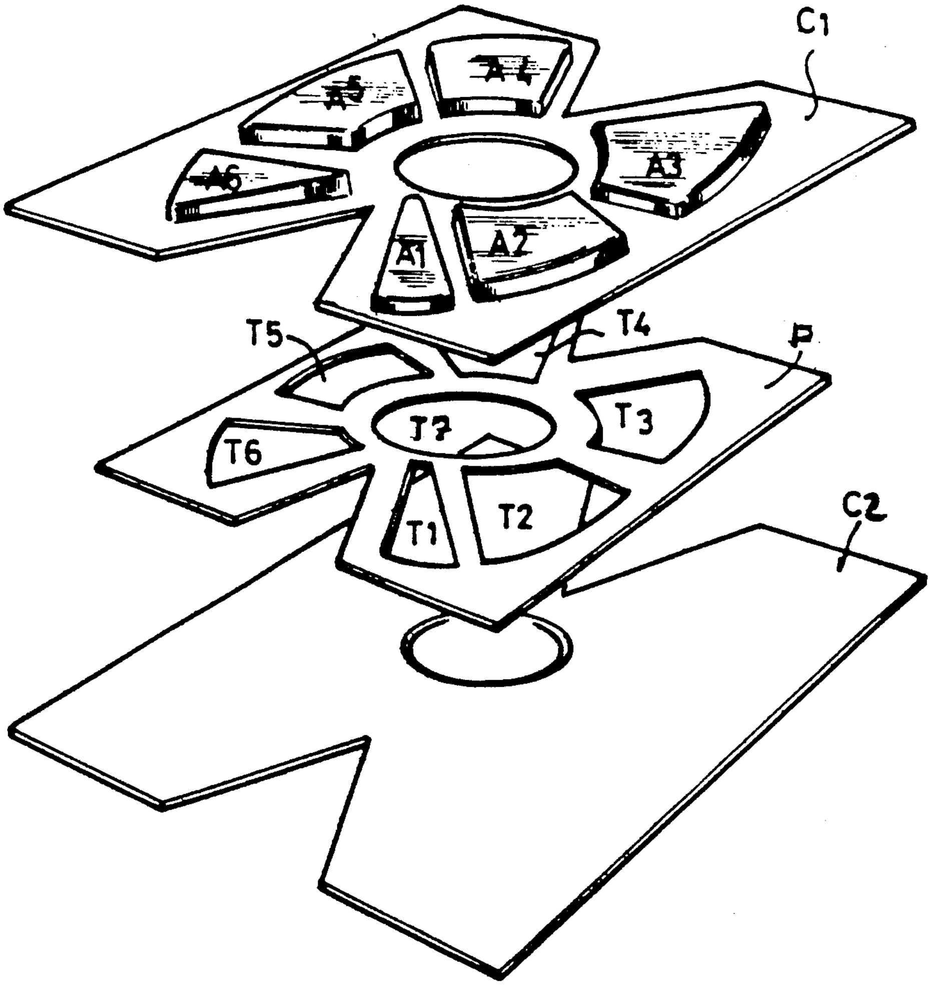
FIG. 2 is an exploded view showing the various elements of the invention mask of FIG. 1.

As can be seen in FIG. 2, shell C consists of a chamber initially made of three plane layers. There is outside layer C1 of unwoven materials of shrinkable fibers, such as polyvinyl fibers, intermediate plate P made of a semi-rigid PVC film and inside layer C2 of antiallergy food-grade polyvinyl. Outside layer C1 is preformed with recesses (A1–A2, etc.) as mentioned above. Intermediate plate P is cut out with holes T1 to T6 (optionally T7) corresponding in shape, number and arrangement to the recesses of layer C1. However, the dimensions of these holes are smaller than those of the corresponding recesses for reasons that are explained below. Layer C2 is not pierced.

Layer C1 being laid flat, with the open sides of the recesses facing outward, is filled entirely with activated carbon (or any other similar filtering material). Intermediate plate P is placed on top, its holes being made to coincide with the recesses. Then layer C2 is laid on of both. A flat heat-sealing is performed to close the recesses.

Because openings T1–T2, etc., are smaller than the bases of these recesses, the air coming into this zone is deflected to the activated carbon before being able to reach the inside of the mask. After Vs have been cut out, shaping is performed by suitable heat-sealings.

The heat input necessary for this shaping and fastening the various layers together, at the same time produces the shrinking of the three layers, which has the effect of compressing the activated carbon between layer C1 limiting the recesses and closing layer C2.

Optionally, the central recess can be replaced by suction valve 3 which is then assembled in a standard way.

Filled with activated carbon, the resultant mask can be used, among other things, for protection from nonfibrogenous dusts without particular toxicity, from organic vapors whose boiling point is above 60° C. and from acid vapors, such as, sulfurous and sulfuric anhydride, nitrogen oxides, halogen acids: hydrochloric, hyrobromic, hydriodic, and hydrogen acids: hydrogen sulfide, mercaptans, and in general everywhere nonfibrogenous dusts constitute an annoyance for the user with emission of organic or acid vapors and in particular from polyurethane and isocyanate vapors (when their concentration is less than 0.2 ppm).

What is claimed is:

1. Disposable breathing mask which comprises a shell of several layers of a heat-shrinkable material and a filtering element of a granular material, wherein the granular material is compressed in a plurality of enclosures made up of recesses projecting outwardly on the front face of the outside layer of the mask, occupying almost all of the outer surface of the mask, distributed in the shape of a fan, converging toward a central recess, converging toward an expired air outlet valve and closed by the inside layer of the mask by means of a heat-sealing operation.

2. Disposable breathing mask which comprises a shell of several layers of a heat shrinkable material and a filtering element of a granular material, wherein the granular material is compressed in a plurality of enclosures made up of recesses projecting outwardly on the front face of the outside layer of the mask, occupying almost all of the outer surface of the mask, distributed in the shape of a fan, converging toward a central recess, and wherein, the part of the mask that rests against the face is a heat-sealed flange of polyvinyl, and the entire inside layer consists essentially of polyvinyl, and the mask further contains a semirigid intermediate plate of polyvinyl material placed between the inside and the outside layers and is provided with holes of a shape and arrangement corresponding to the recesses.

3. Breathing mask according to claim 2 wherein the polyvinyl is a food-grade antiallergy polyvinyl.

4. Breathing mask according to claim 2 wherein the recesses converge toward an expired air outlet valve.

5. Breathing mask according to claim 4 wherein the polyvinyl is a food-grade antiallergy polyvinyl.

6. Breathing mask according to claim 2 wherein the holes of the intermediate plate have dimensions less than those of the base of the corresponding recesses so as to deflect the incoming air in the direction of the granular product.

7. Breathing mask according to claim 6 wherein the polyvinyl is a food-grade antiallergy polyvinyl.

8. Breathing mask according to claim 2 wherein the granular filtering element is activated carbon.

9. Breathing mask according to claim 8 wherein the polyvinyl is a food-grade antiallergy polyvinyl.

10. Disposable breathing mask which comprises a shell of several layers of a heat-shrinkable material and a filtering element of a granular material wherein the granular material is compressed in a plurality of enclosures made up of recesses projecting outwardly in the front face of the outside layer of the mask and occupying almost all of the outer surface of the mask and closed by the inside layer of the mask by means of a heat-sealing operation and wherein the mask contains a semirigid intermediate plate of polyvinyl material between the inside and outside layers of the mask having holes of a shape and arrangement corresponding to the recesses and wherein the holes have dimensions less than those of the base of the corresponding recesses so that incoming air can be deflected in the direction of the granular material.

11. Breathing mask according to claim 10 wherein the recesses are distributed in the shape of a fan.

12. Breathing mask according to claim 11 wherein the recesses converge toward an expired air outlet valve.

13. Breathing mask according to claim 12 wherein the part of the mask that rest against the face is a heat-sealed flange of food-grade antiallergy polyvinyl.

14. Breathing mask according to claim 13 wherein the entire inside layer consists essentially of food-grade antiallergy polyvinyl.

15. Breathing mask according to claim 14 wherein the granular filtering element is activated carbon.

16. Breathing mask according to claim 10 wherein the granular filtering element is activated carbon.

* * * * *